United States Patent [19]

Every

[11] 4,052,503

[45] Oct. 4, 1977

[54] LOW-TEMPERATURE SYNTHESIS OF UREA

[75] Inventor: Richard L. Every, Ponca City, Okla.

[73] Assignee: Continental Oil Company, Ponca City, Okla.

[21] Appl. No.: 31,420

[22] Filed: Apr. 23, 1970

Related U.S. Application Data

[63] Continuation-in-part of Ser. No. 581,189, Sept. 22, 1966, abandoned.

[51] Int. Cl.$^2$ .................... C01C 1/16; C07C 126/00
[52] U.S. Cl. ............................... 423/470; 260/555 R
[58] Field of Search ................ 260/555 R; 423/470, 423/471

[56] References Cited

PUBLICATIONS

Stuer, B. C., Berichte, vol. 38, p. 2326 (1905).

Primary Examiner—James O. Thomas, Jr.
Assistant Examiner—A. Siegel
Attorney, Agent, or Firm—Richard W. Collins

[57] ABSTRACT

Urea is produced by reacting phosgene and ammonia, one of the reactants being in the liquid state and the other gaseous, at −50° to −20° C.

8 Claims, No Drawings

LOW-TEMPERATURE SYNTHESIS OF UREA

STATUS OF RELATED APPLICATIONS:

This application is a continuation-in-part of co-pending U.S. Ser. No. 581,189, filed Sept. 22, 1966 now abandoned.

This invention relates in general to the synthesis of urea. More specifically it relates to the preparation of urea by reacting phosgene and ammonia.

Urea is useful as a high nitrogen, slow release fertilizer. In contrast to other nitrogen fertilizers, it is resistant to leaching from soil, is noncorrosive to equipment used in application, and is not phytotoxic when applied to plant leaves in a spray. Urea also finds use as a protein supplement for cattle and in the production of urea formaldehyde resins.

Ammonia and phosgene are thought to react thus to produce urea:

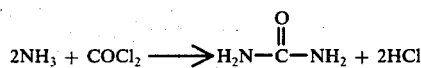

and the resulting HCl to react with more ammonia so that the resulting over-all reaction is:

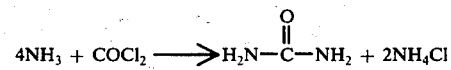

British Pat. No. 245,768 discloses the reaction of phosgene and ammonia at temperatures between 60° and 80° C to make a fertilizer product containing urea and ammonium chloride as principal components. The phosgene and the ammonia can be dissolved in a solvent such as chloroform, acetone, or benzene.

I have observed that when phosgene and ammonia are reacted at room temperature and at higher temperatures the reaction product is a tarry, malodorous material which requires extensive treatment to extract the urea present. As pointed out in the British patent, if the phosgene is added in excess of that stoichiometrically necessary, other nitrogeneous compounds are formed such as cyanuric acid, cyanamide, and ammelide. The British patent is concerned primarily with the preparation of a fertilizer material per se which is high in urea content but which, in addition to ammonium chloride, may well contain quantities of other nitrogenous material, particularly if an excess of phosgene is reacted.

I have discovered that a greatly improved yield of urea can be obtained by directly reacting phosgene and ammonia at temperatures between $-70°$ and about $-20°$ C and at about atmospheric pressure. Preferably I prefer to react the two compounds at temperatures between about $-50°$ and about $-20°$ C. I may incorporate the ammonia into a suitable solvent for reaction purposes if such is desirable, such as methanol, water, or chloroform.

The process according to the present invention can be carried out by liquefying either the ammonia or the carbonyl chloride and bubbling through it the other reactant. At atmospheric pressure or less, phosgene is a liquid between the temperatures of $-118°$ and 80° C, and ammonia between about $-78°$ and $-33°$ C. In some cases it may be desirable to liquefy both reactants and add one to the other at a temperature in the above-recited ranges. The preferred method, however, is first to liquefy the ammonia and then through it introduce gaseous phosgene. The gaseous phosgene is continually passed through the liquid ammonia until the effluent gas from the reaction indicates no further consumption of phosgene. The reaction between the liquid ammonia and gaseous phosgene proceeds rapidly with the evolution of heat. It therefore is necessary to cool the reaction mixture to maintain it at the desired cryogenic temperature.

The following examples will further illustrate the nature of my invention, which, however, is not limited thereto.

EXAMPLE I

About 100 milliliters of commercial grade liquid ammonia (containing about 0.1% water) was placed in a 300-ml test tube maintained at $-50°$ C by a bath made up of acetone and solidified carbon dioxide (Dry Ice). Gaseous phosgene (CP grade) from a compressed gas cylinder was then introduced into the liquid ammonia. A vigorous exothermic reaction occurred. The reaction was continued by adding more phosgene until no more phosgene was consumed. The resulting product was determined to be 39 weight percent urea and 61 weight percent ammonium chloride. On the basis of the ammonium chloride produced, the yield of urea was about 108 percent of theoretical.

EXAMPLE II

In this test a volume of liquid phosgene was completely reacted with gaseous ammonia at a temperature of $-50°$ C. Again a vigorous exothermic reaction occurred. The resulting product was determined to be 27 weight percent urea and 73 weight percent ammonium chloride. The yield was about 75 percent of theoretical.

EXAMPLE III

In this test 100 milliliters of anhydrous liquid ammonia (dried over sodium) was completely reacted with gaseous phosgene at a temperature of $-50°$ C. Again a vigorous exothermic reaction was observed and the resulting product was determined to be 48 weight percent urea and 52 weight percent ammonium chloride. On the basis of the ammonium chloride produced, the yield was 133 percent of theoretical.

EXAMPLE IV

In this test 17 grams of ammonia was dissolved in 50 milliliters of alcohol. Gaseous phosgene was then bubbled through the solution while the reaction mixture was maintained at $-50°$ C. In this test the effluent gas was passed over moistened blue litmus paper which turns pink when phosgene is present. When the litmus paper turned pink, the reaction was discontinued. The reaction product obtained analyzed 25 weight percent urea and 75 weight percent ammonium chloride, corresponding to a yield based on the ammonium chloride produced of about 70 percent of theoretical.

In Examples I and III the theoretical yield based on the amount of ammonium chloride produced is above 100 percent. This is thought to result because some of the HCl generated during the reaction did not react with ammonia present to yield additional ammonium chloride, but was evolved from the system as HCl. In each of the foregoing Examples the reaction product obtained as a white crystalline material. In Examples I, II, and III the reaction product could be extracted of the urea by methanol.

In other tests, ammonia was dissolved in methanol, water, chloroform, benzene, and acetone and reacted with gaseous phosgene at temperatures between 0° and 25° C (room temperature). A tarry, malodorous product was obtained at the higher temperatures which showed evidences of containing cyanamide and other undesirable (or nonurea-type) compounds, indicating that a less pure, less desirable reaction product is obtained in the reaction of phosgene and ammonia at higher temperatures.

EXAMPLE V

Phosgene was added to ammonia in a closed reaction system at the desired temperature. After the reaction was completed, any unreacted material was allowed to vaporize at ambient temperature and the product was weighed and analyzed. There was some difficulty encountered with inlet lines becoming clogged with reaction product at the two lowest temperature runs, causing somewhat erratic results on the amount of product produced. The data obtained in the study are shown in Table I.

TABLE I

| Temperature of Reaction ° C | Urea-NH$_4$Cl Yield % | Side Product by X-ray[a] Chart Divisions | |
|---|---|---|---|
| | | 4.28 A ° | 2.93 A ° |
| −50 | 29 | 3.7 | 31.2 |
| −40 | 18 | 2.6 | 19.2 |
| −35 | 57 | 3 | 34 |
| −25 | 34 | 3.5 | 38 |
| −20 | 24 | 4.2 | 32.2 |
| −15 | 24 | 16.5 | 54.5 |
| 0 | 15 | 100+ | 64.0 |

[a]Side product unidentified, but it is not cyanamide or cyanuric acid.

It can be seen from the data in the Table that impurities remain at a low level and relatively constant to about −20° C, and above this reaction temperature increase rapidly.

Reasonable variation and modification are possible within the scope of the foregoing disclosure and the appended claims to the invention, the essence of which is a method of synthesizing urea, comprising reacting phosgene and ammonia at temperatures broadly in the range of about −70° C to about −20° C, and preferably in the range of about −50° C to about −20° C.

What is claimed is:

1. A process for producing urea and ammonium chloride in high yield with a low level of impurities comprising combining as reactants phosgene and ammonia at a temperature in the range of about −70° C. to about −20° C. by adding one reactant to the other and maintaining the combination in said temperature range.

2. A process of claim 1 in which the temperature range is about −50° C. to about −20° C.

3. The process of claim 2 wherein said ammonia is reacted in a gaseous state with said phosgene in a liquid state.

4. The process of claim 2 wherein said phosgene is reacted in a gaseous state with said ammonia in a liquid state.

5. The process of claim 2 wherein said ammonia is dissolved in a carrier solvent selected from a group consisting of methanol, water, and chloroform.

6. The process of claim 2 wherein said ammonia is dissolved in methanol.

7. A process for producing a reaction product consisting essentially of urea and ammonium chloride comprising (a) contacting ammonia with phosgene, one of said ammonia and phosgene being in the liquid state and the other being in the gaseous sate, and (b) maintaining the temperature of the resulting reaction mixture between about −50° C and about −20° C.

8. A process for producing a reaction product consisting essentially of urea and ammonium chloride comprising (a) contacting ammonia with phosgene, one of said ammonia and phosgene being in the liquid state and the other being in the gaseous state, and (b) maintaining the temperature of the resulting reaction mixture at about −50° C.

* * * * *